United States Patent [19]

Perretti et al.

[11] Patent Number: 5,229,367

[45] Date of Patent: Jul. 20, 1993

[54] ANTIINFLAMMATORY PEPTIDE DERIVED FROM HUMAN LIPOCORTIN V

[75] Inventors: Mauro Perretti, Florence; Cristina Becherucci, Santa Fiora; Kenneth G. Mugridge, Casciano di Murlo; Egle Solito, Monteriggioni; Rivo Presentini; Luca Parente, both of Siena, all of Italy

[73] Assignee: Sclavo S.p.A., Milan, Italy

[21] Appl. No.: 642,840

[22] Filed: Jan. 18, 1991

[51] Int. Cl.$^5$ ............... A61K 37/64; A61K 37/02; C07K 7/06
[52] U.S. Cl. ........................... 514/15; 514/2; 530/300; 530/328
[58] Field of Search ............ 514/2, 15; 530/300, 530/328

[56] References Cited

U.S. PATENT DOCUMENTS 4,895,931  1/1990  Okazaki et al. ............ 530/326
5,081,019  1/1992  Wallner et al. ............ 435/69.2

OTHER PUBLICATIONS

Devereaux et al., 12 Nucleic Acid Res. 387–395 (1984).
Cirino et al., 86 Proc. Natl. Acad. Sci. USA 3428–3432 (1989).
Cirino et al., 166 Eur. J. Pharmacol. 505–510 (1989).
K. S. Huang et al., *Journal of Biological Chemistry* 262:7639–7645, Jun. 5, 1987.
B. P. Wallner et al., *Nature* 320:77–81, Mar. 6, 1986.
L. Miele et al., *Nature* 335:726–730, Oct. 20, 1988.

*Primary Examiner*—Robert A. Wax
*Assistant Examiner*—Stephen Walsh
*Attorney, Agent, or Firm*—Birch, Stewart, Kolasch and Birch

[57] ABSTRACT

The synthetic peptide of formula (I) H-Ser-His-Leu-Arg-Lys-Val-Phe-Asp-Lys-OH (SEQ ID NO. 1) and its physiologically acceptable organic or inorganic salts are novel. The synthetic peptide (I), whose amino acid sequence corresponds to that of the sequence 204-212 of human lipocortin V, shows in vitro the capability of inhibiting the prostaglandin E2 release and in vivo an antiinflammatory activity. The peptide and its organic and inorganic salts are useful as therapeutic agents for the treatment of dermatological and collagen inflammatory infections.

4 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Ser His Leu Arg Lys Val Phe Asp Lys
1               5

ANTIINFLAMMATORY PEPTIDE DERIVED FROM HUMAN LIPOCORTIN V

The present invention relates to a synthetic peptide and to its physiologically acceptable organic and inorganic salts with an in vivo biological activity of antiinflammatory type. Particularly, the present invention relates to the synthetic peptide having an amino acid sequence corresponding to that of the segment 204-212 of lipocortin V. Moreover the invention relates to the use of said synthetic peptide and its organic and inorganic salts as therapeutic agents for the treatment of dermatological and collagen inflammatory infections, and relates to pharmaceutical compositions comprising the same. A continuously increasing amount of experimental data has shown that the metabolism products of arachidonic acid (AA), i.e. prostaglandins, hydroxyacids and leukotrienes exhibit many strong biological activities. In particular, said products, also known as eicosanoids, are involved in the appearance of inflammatory reactions. The phospholipase A2 (PLA2) is the enzyme which releases the AA from the cellular membrane phospholipids and makes it available to the successive metabolism by the cyclooxygenase and lipoxygenase enzymes, with formation of said substances with proinflammatory action. The importance of controlling the PLA2 activity is thus evident. Flower et al. (Br. J. Pharmacol. 87: 57-62, 1986) and Hirata et al. (Adv. Inflammation Res. 7: 71-78) reported some years ago the existence of an in vivo control of such an inflammatory process through the production, in different cell-types, of structurally correlated proteins induced by the endogenous steroids. Said proteins are also known under the general term of lipocortins, and exhibit antiinflammatory activity relative to their capability of impairing phospholipase A2 (Di Rosa et al. Prostaglandins, 28: 441-442, 1984). Moreover the in vitro antiphospholipase and the in vivo antiinflammatory activities have been proved for many natural lipocortins in different experimental models (Blackwell et al. Br. J. Pharmacol. 76: 185-194, 1982; Parente et al. Eur. J. Pharmacol. 99: 223-239, 1984; Parente et Flower, Life Sci. 36: 1225-1231, 1985). In contrast to the known compounds (corticosteroids and non-steroid substances) used at present as antiinflammatories, lipocortins inhibit the production of substances with inflammatory activity through the control of the phospholipase activity, without inducing undesirable side effects. Therefore said proteins represent excellent agents for the treatment of inflammatory occurrences in humans. However, the use of natural lipocortins has drawbacks due to their limited availability. Recently the amino acid sequence of six recombinant proteins correlated to lipocortins have been published (Huang et al. J. Biol. Chem. 262: 7639-7645, 1987; Pepinsky et al. J. Biol. Chem. 263: 10799-10811, 1988). All these proteins have in vitro antiphospholipase activity; moreover the effectiveness as an in vivo antiinflammatory has already been reported for lipocortin I (Cirino et al. Proc. Natl. Acad. Sci. USA, 86: 3428-3432, 1989). Still more interesting, in the present context, is the recent description of a nine amino acid fragment of human lipocortin I showing in vitro antiphospholipase and in vivo antiinflammatory activity (Miele et al. Nature, 335: 726-730, 1988). Said peptide has been identified on the basis of the similarities between the amino acid sequences of human lipocortin I and rabbit uteroglobin, both of which inhibit PLA2 in vitro. Peptide (I) herein disclosed has been identified by using the same criterion; in fact, by matching the amino acid sequences of uteroglobin (Miele et al. supra) and human lipocortin V (Pepinsky et al. supra) a high homology domain between the two proteins has been detected with the Best Fit program: i.e., a domain corresponding to lipocortin V is comprised within the peptide (I). This peptide likely corresponds, at least in part, to the active site of lipocortin V. On the other hand a more precise identification of the biological site of a protein, specifically of the PLA2 inhibiting active site of the human lipocortin V, is particularly desirable for the following reasons: firstly, it would enable a deeper understanding of the mechanisms of the protein activity; secondly, because a peptide with a shorter amino acid sequence than the native protein would be easier to prepare and/or purify by making use of conventional chemical synthesis or recombinant DNA techniques. Such a peptide needs, however, to exhibit the desired biological activity not only in vitro, but in vivo as well.

An object of the present invention is therefore a synthetic peptide having the amino acid sequence corresponding to the one of the human lipocortin V phospholipase A2 inhibiting active sites, capable of in vitro inhibition of PLA2 activity, and exhibiting in vivo antiinflammatory activity. A further object of the present invention is the use of said synthetic peptide, and of physiologically acceptable organic and inorganic salts thereof, as reagents for the treatment of inflammatory infections. A still further object of the present invention is a pharmaceutical composition comprising a therapeutically effective amount of said peptide or of organic and inorganic salts thereof, for treating inflammatory infections. Further objects of the present invention will be evident from the text and examples which follow.

In particular, the synthetic peptide according to the present invention shares the amino acid sequence of the segment 204-212 of the human lipocortin V defined by the formula: H-Ser-His-Leu-Arg-Lys-Val-Phe-Asp-Lys-X (SEQ I.D. NO. 1); where Ser=L-serine, His=L-histidine, Leu=L-leucine, Arg=L-arginine, Lys=L-lysine, Val=L-valine, Phe=L-phenylalanine, Asp=L-aspartic acid, X=OH. By the term "synthetic" is meant a peptide not present in nature as such, but obtainable by chemical synthesis or by the use of recombinant DNA techniques. Preferably, the peptide of the present invention is prepared by chemical synthesis, since this method, in contrast to the recombinant DNA techniques, enables the production of a product that is not fused, i.e. comprising no sequences foreign to the human lipocortin V, and which can be easily purified. The synthesis of peptide (I) of the present invention may be carried out by following one of the general techniques known and applied in this specific field of chemistry. According to the present invention the synthetic peptide (I) was synthesized on a solid phase as described by Merrifield et al. in "The Proteins" 3rd Edition, Vol. II, pp 255-527 (1976). In general said method comprises:

a) condensing a first amino acid, alpha-amino protected, upon a solid insoluble support by esterifying its terminal carboxylic salt group to the functional linking group of the solid support;

b) removing the protective group from the alpha-amino residue;

c) condensing the amino acid immobilized on the solid support to a second amino acid, alpha-amino protected as reported in item (a), by reacting the now unprotected amino group of the first amino acid with the carboxylic group of the second amino acid;

d) removing the alpha-amino protecting group from the second amino acid;

e) condensing the other amino acids in progression according to the scheme reported in (b) through (d) until the desired peptide sequence is obtained;

f) cleaving the thus synthesized peptide from the solid insoluble support and purifying it by chromatography.

At each stage of the aforementioned procedure the solid support bearing the growing peptide chain is collected by filtration and thoroughly washed to remove the insoluble impurities. Suitable supports for the purpose of the present invention are e.g. polystyrene resins crosslinked with divinylbenzene, phenolic and polyamidic resins. Preferably polystyrenic resins crosslinked with about 1%-2% divinylbenzene, activated with dichloromethyl, and having a final chlorine content of about 1 milliequivalent per g of resin are used. Protecting groups for the alpha-amino group are generally selected from among benzyloxycarbonyl, triphenylmethyl, t-amyloxycarbonyl, 2-nitrophenylsulfanyl, fluorenylmethyloxycarbonyl (Fmoc) and terbutyloxycarbonyl (Boc). Among these, the groups Fmoc and Boc are particularly suitable for the purpose of the present invention, since they are removable under mild operating conditions.

The reactive functional groups present on side chains are generally protected with protecting groups known in peptide synthesis. Generally, protecting groups are employed which are stable under the conditions of removal of the alpha-amino protective group. Protective groups particularly suitable are: for lysine the orthobenzyloxycarbonyl group (Z), and for aspartic acid the benzylester group. The side chain protective groups are removed contemporary with the cleavage of the peptide from the resin. The esterification reaction in stage (a) of the process of the present invention is carried out in a liquid phase of an inert organic solvent in the presence of potassium iodide. The operating temperature is comprised between 30° and 60° C., preferably at a temperature of 50° C. In stages (c) and (e) of the process of the present invention the amino acids are inserted in the growing peptide chain in the form of symmetric anhydrides. Generally said anhydrides are prepared by reacting in an inert organic solvent the suitably protected amino acid with dicyclohexylcarbodiimmide (DCC) at a temperature comprised between $-10°$ and $+30°$ C.; in particular at 0° C. for a period of 10 to 30 minutes and at room temperature (20°-25° C.) for 5 to 10 minutes. The Asp amino acid is added in the form of the p-nitrophenylester operating in an organic solvent in the presence of equimolar amounts of hydroxybenzotriazole. Examples of organic solvents suitable for the purpose of the present invention are aliphatic chlorinated hydrocarbons, dimethylformamide and dimethylacetamide. The removal of the synthetic peptide residue according to the present invention can be carried out by acid or alkaline hydrolysis, aminolysis or alcoholysis. Peptide (I) of the present invention can be isolated and purified by conventional techniques such as high pressure liquid chromatography, precipitation from organic solvents and lyophilization. Synthetic peptide (I) according to the present invention can form salts with organic and inorganic bases. Said salts include ammonium salts, salts of an alkali metal of such as sodium or potassium, salts of alkali-earth metals, such as calcium or magnesium, or salts with organic bases such as dicyclohexylamine, N-methyl-D-glucamine and the like. Non-toxic physiologically acceptable salts are preferred, though other salts are also useful, for example for the isolation and purification of the product. The salts are prepared conventionally by reacting synthetic peptide (I) with one or more equivalents of the selected base in a solvent or medium in which the salt is insoluble, or in water which is eventually removed by drying. The biological activity of peptide (I) of the present invention has been assayed in vitro by means of the inhibition of prostaglandin E2 production in peritoneal rat leukocytes (example 1) and in human fibroblasts (example 2), as well as by inhibition of the contraction of a rat stomach strip induced by phospholipase A2 (Example 3). The obtained results show a significant inhibiting activity of the synthetic peptide of the present invention. The in vivo antiinflammatory activity has been determined by means of the inhibition assay of the oedema in rat paw induced by the the phospholipase A2 (example 4) and by carrageenin (example 5). The obtained results show, in both models, that the synthetic peptide (I) effects a significant oedema inhibition and that said inhibition is dose-dependent. The synthetic peptide (I) can thus be assumed to exhibit antiinflammatory activity, presumably as the consequence of a PLA2 impairment. Therefore, said peptide and organic and inorganic salts thereof are particularly useful for treating inflammatory states in humans. The synthetic peptide according to the present invention and its organic and inorganic salts can be used in the form of conventional pharmaceutical compositions. Said compositions may comprise, in addition to a therapeutically effective amount of the peptide and/or of salts thereof, organic and inorganic materials selected from among those used for internal administration. Moreover said pharmaceutical compositions may comprise materials such as water, vegetable oils, polyalkylene glycols, and the like. Further, to said compositions may be added additives selected from those generally applied in the pharmaceutic domain, such as e.g. stabilizing and emulsifying agents, buffers, and preservatives. The synthetic peptide according to the present invention and its salts or pharmaceutical compositions comprising the same may be given by oral, intravenous, or parenteral administration, in one single dose or in subsequent doses, at a concentration dependent on the seriousness of the case, and in any case generally comprised between 1 and 10 mg/Kg body per day.

The examples which follow illustrate the invention without, however, limiting it.

EXAMPLE 1

Use of the synthetic peptide 204-212 as an in vitro inhibitor of the release of prostaglandin E2 in rat peritoneal leukocytes Rat peritoneal leukocytes were collected and purified as described by Parente and Flower (supra), then suspended in Krebs solution oxygenated with Carbogen at a final concentration of $1.10^6$ cells/ml. Samples (1 ml) of said suspension were incubated in a thermostatic bath at 37° C. for 30 min in the presence (100 $\mu$g/ml) and in the absence (control) of the synthetic peptide 204-212. The incubation was maintained for a further 60 min at 37° C. after addition to each culture of 200 $\mu$g/ml Zymosan (activated by opsonization, i.e. incubated with mouse serum for 30 min at 37° C.). At the end of this time the cells were separated from the suspension by centrifugation at 10,000 rpm for 5 min using an Eppendorf centrifuge model 5414. The supernatants thus recovered were analysed by radioimmunoassay to monitor the prostaglandin E2 (PGE2) levels.

The results illustrated in table 1 show that the peptide 204-2 significantly inhibits the PGE2 release.

TABLE 1

| Treatment | PGE2 | Inhibition % |
| --- | --- | --- |
| Control | 253.7 + 22.8 | — |
| Peptide 204-212 100 μg/ml | 129.0 + 16.9(**) | 49.8 |

(**)means a significance of <0.01 (Student t test). The results are expressed as the average of three samples plus standard error.

EXAMPLE 2

Use of the synthetic peptide 204-212 as an inhibitor of prostaglandin E2 release from human fibroblasts Human embryonal fibroblasts obtained as described by Solito and Parent (Br. J. Pharmacol. 96: 656-660, 1989) were suspended in DMEM medium (Dulbecco's modified Eagle medium) containing 10% (w/v) bovine fetal serum to a final concentration of 10,000 cells per ml. Thereafter 0.2 ml of said suspension were placed into each well of a 96 flat bottomed well Cluster dish (firm Costar) and incubated at 37° C. for 72 hours. At the end of said period the cells were washed three times with 0.2 ml medium without serum and then incubated for 60 min at 37° C. as follows:

one part in 0.2 ml DMEM medium without bovine foetal serum (control);

one part in 0.2 ml DMEM medium comprising different final concentrations of peptide 204-212 (from 1 ng/ml to 100 μg/ml). Bradykinin (Sigma) was added thereafter to the final concentration of 1 μM to all the samples, and the incubation was maintained for a further 30 min. Finally the determination of PGE2 in the cell-free supernatants was carried out by making use of a radioimmunoassay. From the results reported in Table 2, it can be appreciated that the peptide 204-212 exerts a significant inhibition attaining high inhibition values (close to 100%), and that this inhibition is concentration dependent. An ED 50 of 1.13 μg/ml was calculated.

TABLE 2

| Treatment | Concentration | Inhibition % |
| --- | --- | --- |
| Peptide 204-212 | 1 ng/ml | 0 |
| Peptide 204-212 | 10 ng/ml | 16 ± 2 |
| Peptide 204-212 | 100 ng/ml | 41 ± 7 |
| Peptide 204-212 | 1 μg/ml | 43 ± 4 |
| Peptide 204-212 | 10 μg/ml | 63 ± 7(*) |
| Peptide 204-212 | 100 μg/ml | 94 ± 6(*) |

(*)shows a significance <0.05 by the t test of Student on the absolute values. The results are expressed as the average of three samples plus standard error.

EXAMPLE 3

Use of peptide 204-212 as an inhibitor of the PLA2 induced contractions in rat stomach strip The rat stomach bottom strip was prepared as originally described by Vane (Br. J. Pharmacol., 12: 344-349, 1957) and suspended in a small bath for resected organs, thermostated at 37° in Krebs solution. After two hours stabilisation in said bath, the stomach reacts to phospholipase A2 stimulation (pig pancreas phospholipase preparation from Sigma) by contracting. These contractions are recorded by means of an isotonic transducer on recorder (Firm Basile). The contracting effect of the PLA2 is concentration-dependent and a concentration of 4.4 μg/ml was used in the experiments with the peptide 204-212. The experiments were carried out as follows:

a) estimation of the stomach contracting effect by the PLA2 at the final concentration of 4.4 μg/ml (control value)

b) after thoroughly washing the strip, peptide (I) was added at the concentration of 20 μg/ml and the effect of the PLA2 was estimated again after 30 min (sample).

From the results reported in Table 3 it can be appreciated that the peptide 204-212 significantly inhibits the extent of the PLA2 induced stomach contractions, exhibiting a clear in vitro antiphospholipase activity.

TABLE 3

| Treatment | Concentration | Inhibition % |
| --- | --- | --- |
| Peptide 204-212 | 20 μg/ml | 60.5 + 7.5(*) |

(*)means a significance <0.05 by the t test of Student on the absolute values. The results are expressed as the average of four samples plus standard error.

EXAMPLE 4

Use of peptide 204-212 as an inhibitor of the PLA2 induced oedema in rat paw

The oedema induced by PLA2 in the rat paw was generated according to the modified technique of Marshall et al. (J. Cell Biochem. suppl. 12 E: S325, 1985). Practically, the enzyme phospholipase A2 (Naja Mocambique), with a specific activity of about 400 units/mg protein, was dissolved into a physiological solution comprising calcium chloride 1 mM to a final concentration of 100 μg/ml. Thereafter samples (0.5 ml) of said solution were diluted 1:1 (v/v) either with a physiological solution as such, or with a physiological solution comprising the synthetic peptide 204-212 at a concentration of 8 mg/ml. The thus obtained solutions were incubated at 37° C. for 15 min. At the end of this incubation period, 0.1 ml of the solutions either comprising 5 μg of PLA2 only, or additionally 400 μg of the synthetic peptide, were injected into the right back paw of male Wistar rats of 200 g weight (thus the synthetic peptide 204-212 was given at a 2 mg/Kg dose). The oedema in the paw was measured by means of a water plesthysomometer 30 and 60 min after the injection. The results reported in Table 4 confirm the in vivo PLA2 inhibiting effect of the peptide 204-212.

TABLE 4

| Treatment | Oedema 30 min | Oedema 60 min |
| --- | --- | --- |
| Peptide 204-212 | 25.4 + 7.7(*) | 25.4 + 7.8(*) |

(*)means a significance <0.05 by the t test of Student calculated on the absolute values. The results are expressed as the average of five samples plus standard error.

EXAMPLE 5

Use of the synthetic peptide 204-212 as an inhibitor of the carrageenin induced oedema in rat The carrageenin induced oedema in the rat paw was generated as disclosed by Parente et al. (Eur. J. Pharmacol., 99: 233-239, (1984). Practically 0.1 ml physiological solution comprising 1% (w/v) lambda carrageenin (Sigma) were injected subcutaneously into the right back paw of male Wistar rats weighing 200 g pretreated as follows: 5 rats (control) were locally inoculated with 100 μl sterile physiological solution; 5 rats were locally injected with 100 μl physiological solution comprising 400 or 100 mg (respectively corresponding to a dose of 2 and 0.5 mg/Kg) synthetic peptide 204-212. The oedema was measured with a water plethysmometer 3 and 4 hours after the carrageenin injection. The results in Table 5 show an inhibition of the oedema due to the peptide 204-212 and moreover that the extent of the inhibition is dose-dependent.

TABLE 5

| Treatment | Oedema 3 hours Inhibition % | Oedema 4 hours Inhibition % |
|---|---|---|
| Peptide 204-212 2.0 mg/Kg | 37.0 ± 3.3(*) | 37.5 ± 10.1() |
| peptide 204-212 0.5 mg/Kg | 22.7 ± 8.3(*) | 13.7 ± 5.1(*) |

(*) () and (*) mean a significance <0.05, <0.01 and <0.005 by the t test of Student on the absolute values. The results are expressed as the average of five samples plus standard error.

expressed as the average of five samples plus standard error.

---

We claim:

1. A synthetic peptide defined by Formula (I):

H—Ser—His—Leu—Arg—Lys—Val—Phe—Asp—Lys—X    (I)
(SEQ. ID No. 1)

wherein Ser is L-serine, His is L-histidine, Leu is L-leucine, Arg is L-arginine, Lys is L-lysine, Val is L-valine, Phe is L-phenylalanine, Asp is L-aspartic acid, and X is OH; and the organic and inorganic physiologically acceptable salts thereof.

2. A pharmaceutical composition comprising the synthetic peptide according to claim 1, in an amount effective for treating inflammatory states in mammals comprising allergic and asthmatic manifestations, dermatological afflictions, inflammatory diseases, and collagen diseases, and a pharmaceutically acceptable carrier.

3. The pharmaceutical composition according to claim 2 wherein said mammals are humans.

4. A method for treating inflammatory states in mammals in need thereof which comprises administering the composition of claim 2 or the composition of claim 3.

* * * * *